US008539994B2

(12) United States Patent
Cuzydlo (10) Patent No.: US 8,539,994 B2
(45) Date of Patent: Sep. 24, 2013

(54) VALVE WITH BIASING MEMBER

(75) Inventor: Michael Cuzydlo, Orchard Park, NY (US)

(73) Assignee: Piramal Critical Care, Inc., Orchard Park, NY (US)

( * ) Notice: Subject to any disclaimer, the term of this patent is extended or adjusted under 35 U.S.C. 154(b) by 825 days.

(21) Appl. No.: 12/496,895

(22) Filed: Jul. 2, 2009

(65) Prior Publication Data

US 2010/0224285 A1 Sep. 9, 2010

Related U.S. Application Data (60) Provisional application No. 61/209,738, filed on Mar. 9, 2009.

(51) Int. Cl.
*B65B 1/04* (2006.01)
*B65B 3/00* (2006.01)
*B67C 3/00* (2006.01)

(52) U.S. Cl.
USPC ........... 141/352; 141/351; 141/346; 141/347; 141/363; 141/364; 141/365; 141/366; 222/501

(58) Field of Classification Search
USPC ................. 141/346, 319, 347, 351, 352, 363, 141/364, 365, 366; 222/501, 514, 518; 137/625.32
See application file for complete search history.

(56) References Cited

U.S. PATENT DOCUMENTS

| 2,584,167 | A | 2/1952 | Sundholm |
|---|---|---|---|
| 2,597,775 | A | 5/1952 | Brown |
| 2,989,091 | A | 6/1961 | Lowenthal |
| 3,216,630 | A | 11/1965 | Stull |
| RE26,193 | E | 4/1967 | Labat |
| 3,326,402 | A | 6/1967 | Randazzo |
| 3,720,352 | A | 3/1973 | Kozlowski |
| 3,744,526 | A | 7/1973 | MacNiel |
| 4,421,297 | A * | 12/1983 | Pongrass et al. ............. 251/310 |
| 4,509,554 | A | 4/1985 | Failla |

(Continued)

FOREIGN PATENT DOCUMENTS

| RU | 2329832 | 7/2008 |
|---|---|---|
| SU | 1678380 | 9/1991 |

OTHER PUBLICATIONS

International Search Report corresponding to International Application No. PCT/US2009/051397 dated Sep. 15, 2009.

(Continued)

*Primary Examiner* — Timothy L Maust
*Assistant Examiner* — Brandon J Warner
(74) *Attorney, Agent, or Firm* — Tarolli, Sundheim, Covell & Tummino LLP (57) ABSTRACT

An apparatus and system for transferring a liquid, such as a liquid anesthetic, from a reservoir to a machine while minimizing the release of the liquid to the surrounding environment. The apparatus can include a frame member defining a frame passage extending from a first end of the frame member to a second end of the frame member and a nozzle connected to the frame member. The nozzle can be moveable between a first position and a second position relative to the frame member, and can define a plug member configured to block the second end of the frame passage when the nozzle is in the first position. The apparatus can further include a biasing member connected to the frame member and the nozzle.

32 Claims, 7 Drawing Sheets

(56) References Cited

U.S. PATENT DOCUMENTS

| | | | |
|---|---|---|---|
| 4,949,875 A | 8/1990 | Kuo | |
| 5,026,924 A | 6/1991 | Cicco | |
| 5,287,898 A | 2/1994 | Falb et al. | |
| 5,381,836 A * | 1/1995 | Braatz et al. | 141/21 |
| 5,427,145 A | 6/1995 | Grabenkort | |
| 5,488,973 A | 2/1996 | Yamamuro | |
| 5,505,236 A * | 4/1996 | Grabenkort et al. | 141/329 |
| 5,609,276 A | 3/1997 | Greatbatch | |
| 5,617,906 A | 4/1997 | Braatz et al. | |
| 5,682,874 A * | 11/1997 | Grabenkort et al. | 128/200.14 |
| 5,687,777 A * | 11/1997 | Dobson et al. | 141/18 |
| 5,915,427 A | 6/1999 | Grabenkort | |
| 6,135,329 A | 10/2000 | Stoneberg et al. | |
| 6,286,505 B1 | 9/2001 | Psaros | |
| 6,296,623 B2 | 10/2001 | Spinello | |
| 6,582,415 B1 | 6/2003 | Fowles et al. | |
| 6,585,016 B1 * | 7/2003 | Falligant et al. | 141/352 |
| 6,758,376 B1 | 7/2004 | Clodfelter et al. | |
| 6,800,786 B1 | 10/2004 | Rozov et al. | |
| 6,817,390 B2 * | 11/2004 | Falligant et al. | 141/352 |
| 7,159,616 B2 | 1/2007 | Watson et al. | |
| 7,546,856 B2 | 6/2009 | Chotenovsky | |
| 2006/0130930 A1 | 6/2006 | Turker et al. | |
| 2007/0066955 A1 | 3/2007 | Sparholt et al. | |
| 2007/0131725 A1 * | 6/2007 | Friedman | 222/518 |
| 2007/0199616 A1 * | 8/2007 | Chotenovsky | 141/351 |
| 2007/0204931 A1 * | 9/2007 | Freed et al. | 141/351 |
| 2007/0204932 A1 * | 9/2007 | Freed et al. | 141/352 |
| 2008/0302836 A1 | 12/2008 | Mathis | |
| 2009/0260627 A1 | 10/2009 | Cuzydlo et al. | |
| 2010/0018528 A1 | 1/2010 | Cuzydlo | |
| 2010/0018607 A1 * | 1/2010 | Cuzydlo | 141/311 R |
| 2010/0108184 A1 | 5/2010 | Cuzydlo | |
| 2010/0199987 A1 | 8/2010 | Cuzyldo | |
| 2010/0199988 A1 | 8/2010 | Cuzyldo et al. | |
| 2010/0199989 A1 | 8/2010 | Cuzyldo et al. | |
| 2010/0199990 A1 | 8/2010 | Cuzyldo | |
| 2010/0319690 A1 | 12/2010 | Cuzydlo | |

OTHER PUBLICATIONS

International Search Report corresponding to International Application No. PCT/US2009/051391 dated Sep. 17, 2009.
International Search Report corresponding to International Application No. PCT/US2009/62465 dated Jan. 14, 2010.
International Search Report corresponding to International Application No. PCT/US2009/62461 dated Feb. 12, 2010.
International Search Report corresponding to International Application No. PCT/US2009/066535 dated Mar. 12, 2010.
International Search Report corresponding to International Application No. PCT/US2010/026317 dated May 19, 2010.
International Search Report corresponding to International Application No. PCT/US2010/038179 dated Aug. 11, 2010.
International Preliminary Report on Patentability corresponding to International Application No. PCT/US2009/051391 dated Feb. 3, 2011.
International Preliminary Report on Patentability corresponding to International Application No. PCT/US2009/051397 dated Feb. 3, 2011.
Search Report TR 10/066 established by Russian Patent Office corresponding to Turkish Application No. 2009/08207 dated Aug. 9, 2010.
Search Report TR 09/591 established by Russian Patent Office corresponding to Turkish Application No. 2009/07308 dated Jun. 10, 2010.
Search Report TR 10/041 established by Russian Patent Office corresponding to Turkish Application No. 2009/00676 dated Aug. 9, 2010.
Search Report TR 10/130 established by Russian Patent Office corresponding to Turkish Application No. 2009/09123 dated Sep. 14, 2010.
Examination Report TR 08/349 corresponding to Turkish Application No. 2007/03378 dated Jan. 19, 2009.
Examination Report TR 09/551 corresponding to Turkish Application No. 2007/03378 dated May 10, 2010.
Office Action Dated Mar. 7, 2012 in U.S. Appl. No. 12/274,819, Confirmation No. 1977.
Office Action Dated Sep. 26, 2011 in U.S. Appl. No. 12/274,819, Confirmation No. 1977.
International Search Report corresponding to International Application No. PCT/US09/62460.
Office Action Dated Apr. 27, 2012 in U.S. Appl. No. 12/608,081, Confirmation No. 5812.
Office Action Dated May 16, 2012 in U.S. Appl. No. 12/608,092, Confirmation No. 5825.
Office Action Dated May 23, 2012 in U.S. Appl. No. 12/630,174, Confirmation No. 9260.
Office Action Dated May 23, 2012 in U.S. Appl. No. 12/631,936, Confirmation No. 2889.
International Search Report corresponding to International Application No. PCT/US09/66920.
Office Action Dated Oct. 11, 2012 in U.S. Appl. No. 12/608,092, Confirmation No. 5825.

\* cited by examiner

VALVE WITH BIASING MEMBER

CROSS-REFERENCE TO RELATED APPLICATION

This application claims the benefit under 35 U.S.C. §119 (e) of the earlier filing date of U.S. Provisional Application Ser. No. 61/209,338 filed on Mar. 9, 2009, the entire disclosure of which is hereby incorporated by reference herein as if being set forth in its entirety.

FIELD OF THE INVENTION

This application discloses an invention which is related, generally and in various embodiments, to a device for supplying a liquid to a machine, such as a vaporizer.

BACKGROUND OF THE INVENTION

Liquid anesthetics are often packaged in glass bottles and shipped to a location where they may be used to anesthetize a patient undergoing a medical or dental procedure. Such anesthetics may also be used to induce analgesia in a patient undergoing a medical or dental procedure. In order to administer the anesthetic, the contents of the glass bottle are placed in a vaporizer. The vaporizer can vaporize the anesthetic and provide the vaporized anesthetic in a desired amount to the patient.

Inhalable anesthetics are typically volatile substances with relatively low boiling points and high vapor pressure. Preferably, there is little or no release of anesthetic to the atmosphere during handing. To transfer liquid anesthetic to a vaporizer, however, the bottle containing the vaporizer must be opened. Since it is unwise to expose medical personnel performing a procedure to an anesthetic, and since anesthetics are expensive, devices have been developed to minimize the release of anesthetic from a bottle to the environment surrounding a vaporizer. These devices, however, have failed to effectively minimize the release of anesthetic.

SUMMARY OF THE INVENTION

This application discloses an apparatus and system for transferring a liquid, such as an anesthetic, from a reservoir to a machine while effectively minimizing the release of the liquid to the surrounding environment. The apparatus can include a frame member defining a frame passage extending from a first end of the frame member to a second end of the frame member and a nozzle connected to the frame member. The nozzle can be moveable between a first position and a second position relative to the frame member, and can define a plug member configured to block the second end of the frame passage when the nozzle is in the first position. The apparatus can further include a biasing member connected to the frame member and the nozzle.

DETAILED DESCRIPTION OF THE INVENTION

The accompanying drawings are intended to provide further understanding of the invention and are incorporated in and constitute a part of the description of the invention. The drawings illustrate an embodiment of the invention and together with the description illustrate principles of the invention.

The drawings should not be taken as implying any necessary limitation on the essential scope of invention. The drawings are given by way of non-limitative example to explain the nature of the invention.

For a more complete understanding of the instant invention reference is now made to the following description taken in conjunction with accompanying drawings.

The various features of novelty which characterize the invention are pointed out specifically in the claims which are a part of this description. For a better understanding of the invention, reference should be made to the drawings and descriptive matter in which there are illustrated and described preferred embodiments of invention.

Figure 1:
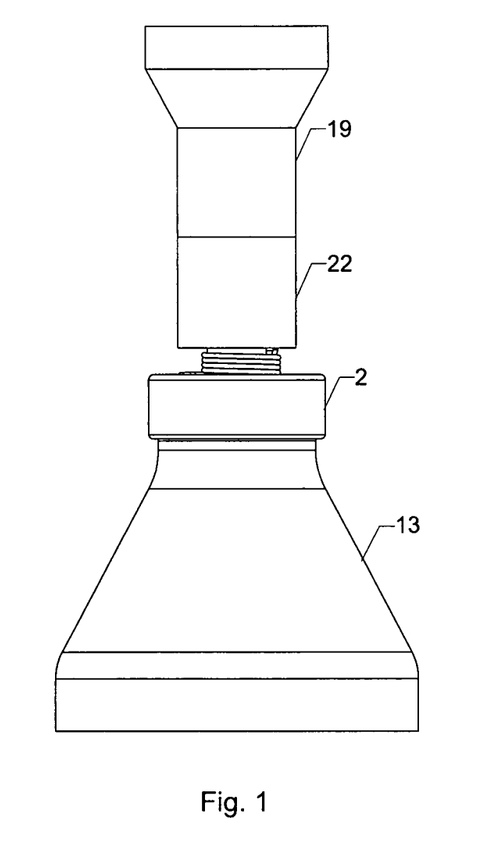
FIG. 1 illustrates a closing mechanism connecting a reservoir to a vaporizer.

Referring now to the drawings, wherein like numerals designate identical or corresponding parts throughout the referred views, FIG. 1 shows various embodiments of an apparatus 22 connecting a reservoir 13 to a machine 19. The reservoir 13 can be a glass bottle or any other container capable of containing a liquid. In this embodiment, the liquid is a volatile anesthetic. At its top, the reservoir 13 includes an opening 16 (see FIG. 5B) through which liquid anesthetic may be transferred from the reservoir 13 to the apparatus 22, and ultimately to the machine 19. In this embodiment, the machine 19 is a vaporizer that dispenses anesthetic to a person undergoing a medical procedure and the apparatus 22 is a closing mechanism connecting the vaporizer 19 the reservoir 13. The reservoir 13 can connect to the closing mechanism 22 by any commonly known method. In this embodiment, the closing mechanism 22 is attached to the reservoir 13 by a gasket 1 (see FIG. 5B) and a crimp band 2. The connection between the closing mechanism 22 and the vaporizer 19 will be discussed in detail later in this description.

Figure 2:
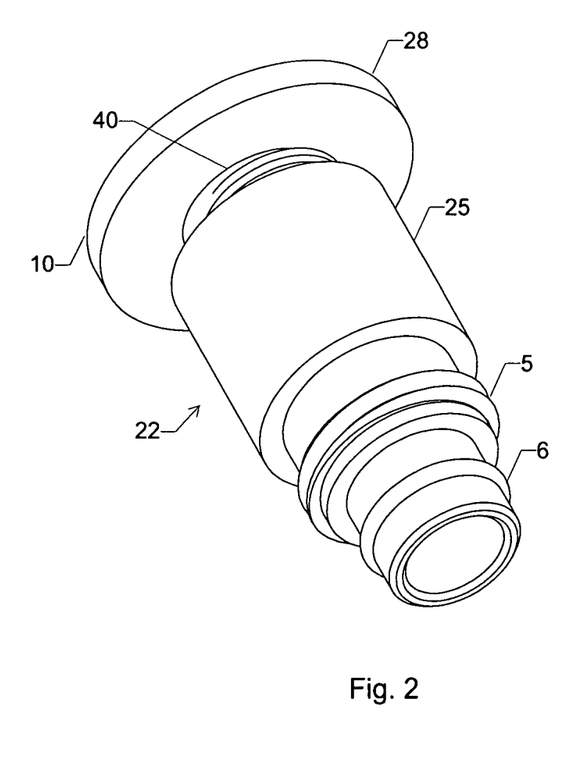
FIG. 2 provides an isometric view of a closing mechanism.

FIG. 2 provides an isometric view of a closing mechanism 22 according to various embodiments for selectively allowing liquid to transfer from a reservoir 13 to a vaporizer 19. The closing mechanism 22 includes a frame member 28 and a nozzle 25. The nozzle 25 is connected to the frame member 28, and the nozzle is moveable between a first position and a second position relative to the frame member 28. The first position of the nozzle can prevent the passage of liquid within the closing mechanism 22 (as shown in FIG. 5B), and the second position of the closing mechanism 22 can allow such passage (as shown in FIG. 6B).

The frame member 28 comprises a base 10 configured for connection to the reservoir 13. As discussed with regard to FIG. 1, the base 10 can be configured for connection to the reservoir by a gasket 1 and crimp band 2, or by any other commonly known method. The opposite end of the frame member 28 can be surrounded by the nozzle 25.

The nozzle 25 is configured for connection to a machine, such as the vaporizer 19. For example, the nozzle 25 can define an external threading 5 for engaging an internal threading of a receiving station 37 of a vaporizer 19. Further, a sealing member 6, such as an O-ring, can be in contact with the nozzle 25 and can allow for a seal between the nozzle 25 and the receiving station 37 of the vaporizer 19.

Figure 3:
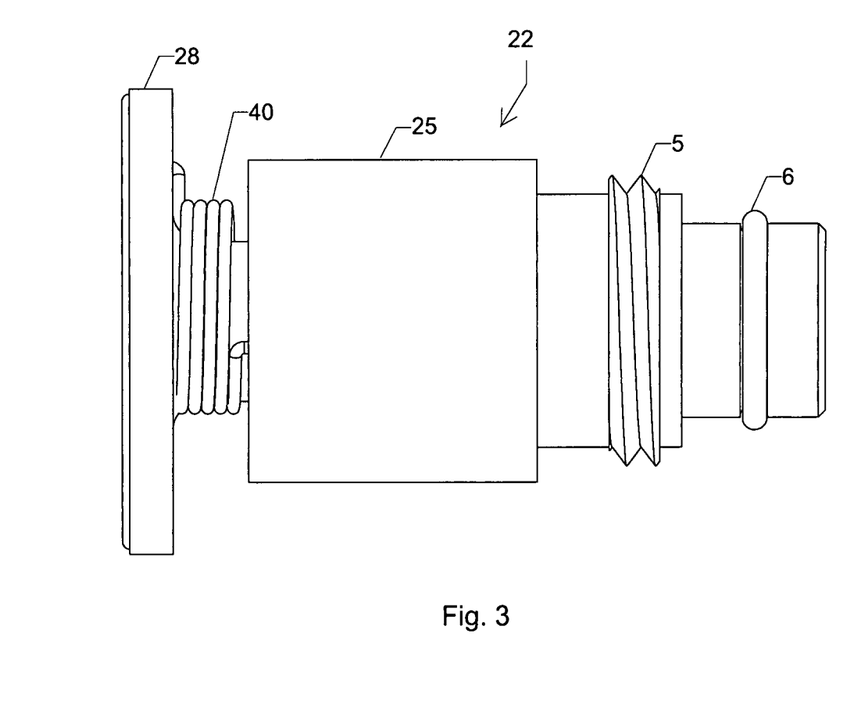
FIG. 3 is a side view of the closing mechanism of FIG. 2.

FIG. 3 shows a side view of the closing mechanism 22. From this view, it is shown that a biasing member 40 can be connected at one end to the base 10 of the frame member 28 and at the opposite end to the nozzle 25. The biasing member 40 can be a spring, such as a torsion spring. As will be discussed in greater detail below, the biasing member 40 can apply a biasing force between the frame member 28 and the nozzle 25 to prevent the flow of a liquid.

Figure 4:
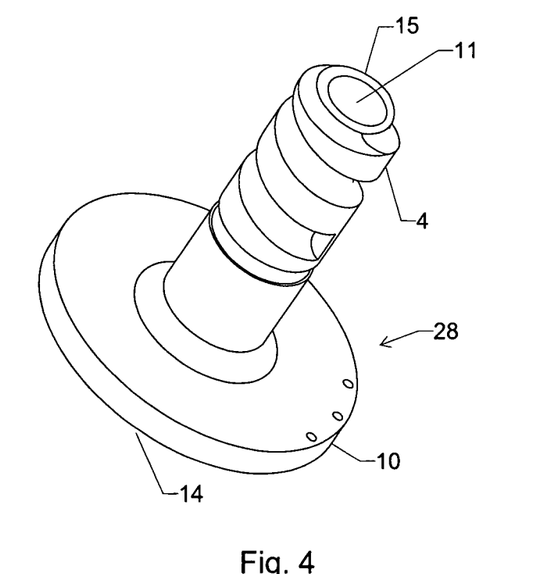
FIG. 4 illustrates the frame member of the closing mechanism of FIG. 2, where the frame member is apart from the nozzle.

FIG. 4 shows the frame member 28 apart from the nozzle 25. From this view, one can observe the base 10 of the frame member 28 and the defining of a threading 4 configured for engagement with the nozzle 25. FIG. 4 further shows a first end 14 of the frame member 28, a second end 15 of the frame member 28, and a frame passage 11 that extends from the first end 14 of the frame member 28 to the second end 15 of the frame member 28. Through the frame passage 11, liquid can flow between the first end 14 and second end 15 of the frame member 28.

Figure 5A:
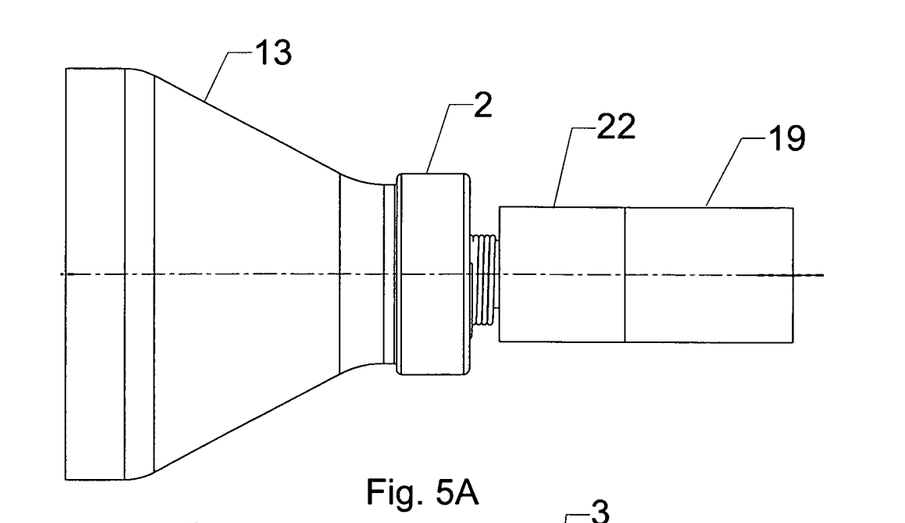
FIG. 5A illustrates the closing mechanism of FIG. 2 connected to a reservoir and a vaporizer, the nozzle pressing the activating rod of the vaporizer.
Figure 5B:
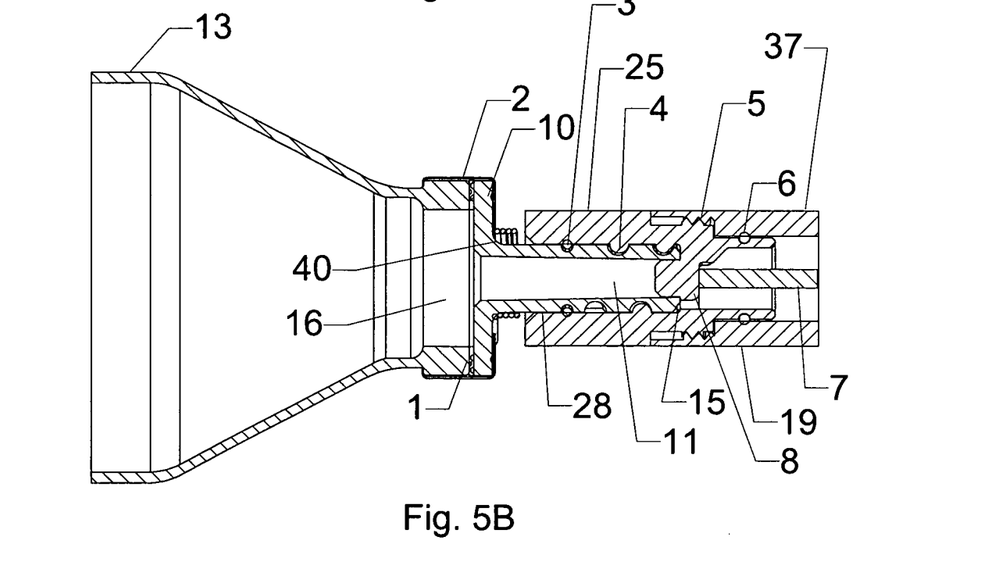
FIG. 5B illustrates the cross section at FIG. 5A's cross axis and shows the first position of the nozzle.

FIG. 5A shows the closing mechanism 22 connected to a reservoir 13 and a vaporizer 19. FIG. 5B shows the cross section at FIG. 5A's cross axis where the nozzle 25 is at the first position such that plug member 8 prevents the passage of liquid within the closing mechanism 22. As previously discussed, the reservoir 13 can connect to the base 10 of the frame member 28 by a standard crimp band 2 and gasket 1 arrangement.

FIG. 5B further shows that the frame member 28 can be threadedly connected to the nozzle 25, where the nozzle 25 and the frame member 28 can respectively define a threading 4 configured for mutual engagement. A sealing member 3 in contact with the frame member 28 and nozzle 25, such an O-ring, can be included to provide a sliding seal between the frame member 28 and the nozzle 25.

The nozzle 25 further defines a plug member 8 configured to block the second end 15 of the frame passage 11 when the nozzle is in the first position, thus preventing the passage of liquid through the frame passage 11, and thus preventing the passage of liquid from the reservoir 13 to the vaporizer 19. The biasing member 40 applies a biasing force between the frame and the nozzle so that the plug member is normally in this first position. The discussion of FIG. 6B below further describes the relationship between the plug member 8 and the biasing member 40.

The external threading 5 of the nozzle 25 allows the closing mechanism 22 to connect with the receiving station 37 of the vaporizer 19. To connect the closing mechanism 22 to the vaporizer 19, a user can apply an initial rotation force to the reservoir 13 (already connected to the closing mechanism 22) such that the nozzle 25 engages the receiving station 37 by the external threading 5. As discussed above, the sealing member 6 allows a seal between the nozzle 25 and the receiving station 37. When the nozzle 25 is fully engaged with the receiving station 37 and can no longer rotate, the plug member 8 of the nozzle 25 has advanced sufficiently that it can press against an activation rod 7 of the receiving station 37, thereby opening the valve of the vaporizer 19.

Figure 6A:
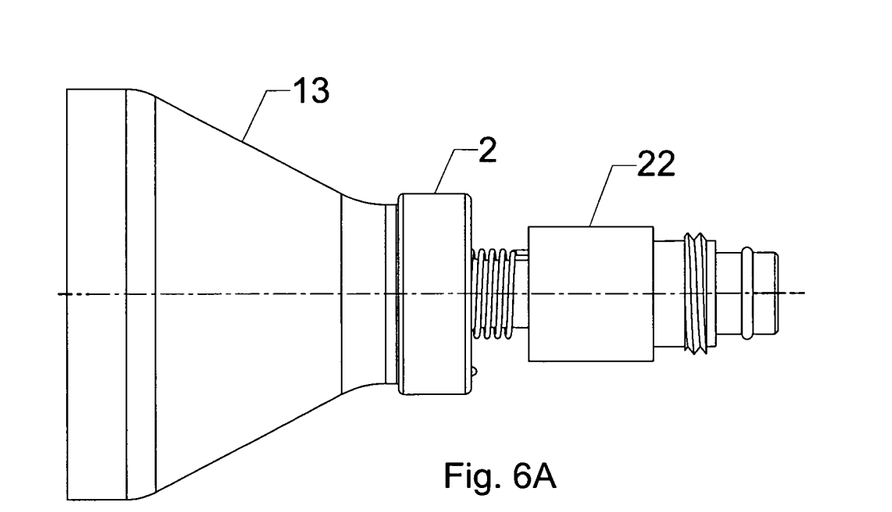
FIG. 6A illustrates the closing mechanism of FIG. 2 and connected to a reservoir, the reservoir opened to the vaporizer.
Figure 6B:
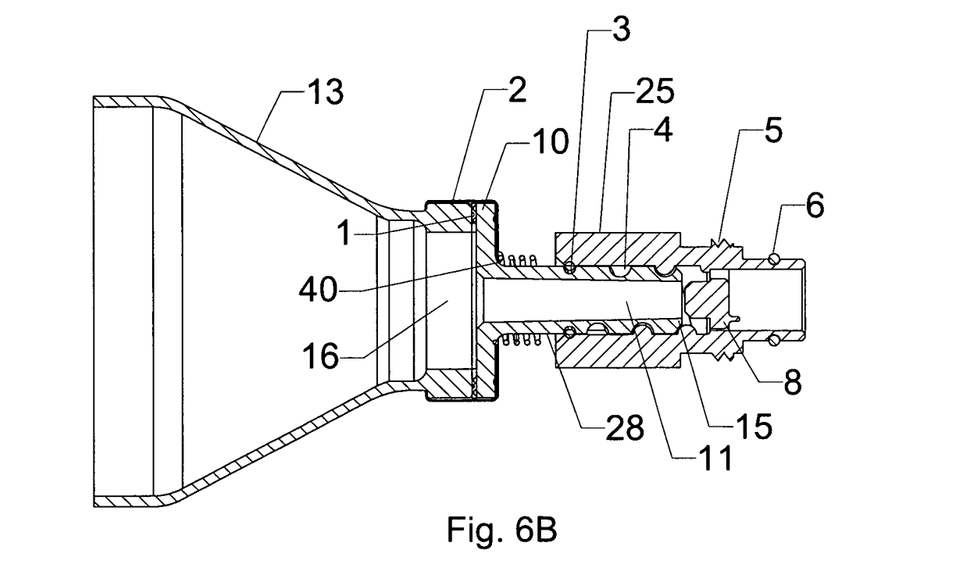
FIG. 6B illustrates the cross section at FIG. 6A's cross axis and shows the second position of the nozzle.

FIGS. 6A and 6B show how the reservoir 13 can be opened to the vaporizer 19. FIG. 6A shows the closing mechanism 22 connected to the reservoir 13. To better illustrate the closing mechanism, the vaporizer 19 is not shown in this figure; however, the vaporizer 13 would be fully engaged with the closing mechanism 22 (as in FIGS. 5A and 5B) before the reservoir 13 was opened to the vaporizer 19.

FIG. 6B shows the cross section at FIG. 6A's cross axis where the nozzle 25 is at the second position such that plug member 8 does not prevent the passage of liquid within the closing mechanism 22. Once the nozzle can no longer rotate with respect to the vaporizer's receiving station 37, a user can apply a continued rotation force to the reservoir 13 suitable to overcome the biasing force of the biasing member 40. When this biasing force is overcome, the frame member 28 begins to rotate with respect to the nozzle 25 by the threading 4. As the reservoir 13 is rotated, the frame member 28 and the nozzle 25 rotate relative to each other such that the nozzle 25 moves to the second position where the plug member 8 no longer blocks the second end 15 of the frame passage 11. At this stage, the frame passage 11 is opened, thus allowing liquid to flow from the reservoir 13 through the closing mechanism 22 to the vaporizer 19.

Figure 7:
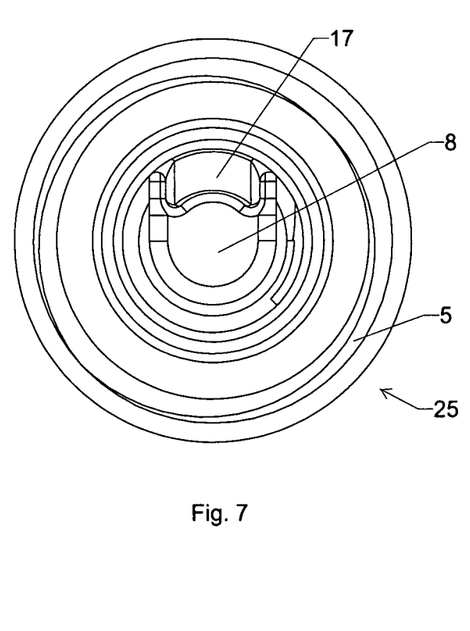
FIG. 7 illustrates a view of the closing mechanism looking into nozzle

Finally, FIG. 7 shows a view of the closing mechanism 22 looking into the nozzle 25. At its center, this view shows the plug member 8 for engaging the activation rod 7. This view also shows a nozzle passage 17 through which liquid from the open frame passage 11 can flow out the nozzle 25 to the vaporizer 19. FIG. 7 also shows the external threading 5 that can engage an internal threading of a receiving station 37 of a vaporizer 19.

It is to be understood that the descriptions of the present invention have been simplified to illustrate characteristics that are relevant for a clear understanding of the present invention. Those of ordinary skill in the art may recognize that other elements or steps are desirable or required in implementing the present invention. However, because such elements or steps are well known in the art, and because they do not facilitate a better understanding of the present invention, a discussion of such elements or steps is not provided herein. The disclosure herein is directed to all such variations and modifications to such elements and methods known to those skilled in the art.

It is to be understood that the invention may assume various alternative orientations and step sequences, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. An apparatus comprising:
   a frame member having a base and a spout, the base adapted to be secured to an opening of a reservoir and the spout having at least one external thread, wherein a through-hole extends through the base and the spout;
   a nozzle having an inner surface with at least one internal thread that is adapted to engage with the at least one external thread on the spout, and an outer surface which is adapted to couple with a machine, wherein the nozzle is moveable between a first position and a second position relative to the frame member;

a plug member fixedly attached to the inner surface of the nozzle, wherein the plug member is adapted to block the through-hole when the nozzle is in the first position; and a biasing member coupled to the frame member and the nozzle to thereby bias the nozzle relative to the frame member.

2. The apparatus of claim 1, wherein the base of the frame member is adapted to be secured to an opening of the reservoir by a gasket and a crimp band.

3. The apparatus of claim 1, wherein the nozzle surrounds the spout.

4. The apparatus of claim 1, wherein the machine is an anesthetic device.

5. The apparatus of claim 1, wherein the outer surface of the nozzle has at least one external thread for engaging with at least one internal thread of the machine.

6. The apparatus of claim 1, wherein the machine is a vaporizer.

7. The apparatus of claim 1, further comprising a sealing member in contact with the nozzle.

8. The apparatus of claim 7, wherein the sealing member is an O-ring.

9. The apparatus of claim 1, further comprising a sealing member in contact with the frame member and the nozzle.

10. The apparatus of claim 9, wherein the sealing member is an O-ring.

11. The apparatus of claim 1, wherein the biasing member is a spring.

12. The apparatus of claim 1, wherein the biasing member biases the frame member relative to the nozzle in a direction causing the nozzle to be in the first position.

13. The apparatus of claim 1, wherein the base of the frame member is crimped on to a reservoir.

14. The apparatus of claim 1, wherein the plug member extends into an aperture formed by the inner surface of the nozzle.

15. The apparatus of claim 1, wherein the nozzle has an aperture defined by an inner surface of the nozzle, and the plug member extends into the aperture to block the through-hole when the nozzle is in the first position.

16. The apparatus of claim 1, wherein the through-hole extends through the nozzle when the nozzle is in the second position.

17. A system, comprising:
a reservoir; and
an apparatus connected to the reservoir, wherein the apparatus comprises:
a frame member having a base and a spout, the base adapted to be secured to an opening of the reservoir and the spout having at least one external thread, wherein a through-hole extends through the base and the spout;

a nozzle having an inner surface with at least one internal thread that is adapted to engage with the at least one external thread on the spout, and an outer surface which is adapted to couple with a machine, wherein the nozzle is moveable between a first position and a second position relative to the frame member;

a plug member fixedly attached to the inner surface of the nozzle, wherein the plug member is adapted to block the through-hole when the nozzle is in the first position; and a biasing member coupled to the frame member and the nozzle to thereby bias the nozzle relative to the frame member.

18. The system of claim 17, wherein the base of the frame member is adapted to be secured to an opening of the reservoir by a gasket and a crimp band.

19. The system of claim 17, wherein the biasing member biases the frame member relative to the nozzle in a direction causing the nozzle to be in the first position.

20. The system of claim 17, wherein the machine is a vaporizer.

21. The system of claim 17, wherein the base of the frame member is crimped on to the reservoir.

22. The system of claim 17, wherein the plug member extends into an aperture formed by the inner surface of the nozzle.

23. The system of claim 17, wherein the nozzle has an aperture defined by an inner surface of the nozzle, and the plug member extends into the aperture to block the through-hole when the nozzle is in the first position.

24. The system of claim 17, wherein the through-hole extends through the nozzle when the nozzle is in the second position.

25. The system of claim 17, wherein the nozzle surrounds the spout.

26. The system of claim 17, wherein the machine is an anesthetic device.

27. The system of claim 17, wherein the outer surface of the nozzle has at least one external thread for engaging with at least one internal thread of the machine.

28. The system of claim 17, further comprising a sealing member in contact with the nozzle.

29. The system of claim 28, wherein the sealing member is an O-ring.

30. The system of claim 17, further comprising a sealing member in contact with the frame member and the nozzle.

31. The system of claim 30, wherein the sealing member is an O-ring.

32. The system of claim 17, wherein the biasing member is a spring.

* * * * *